United States Patent [19]

Okazaki et al.

[11] 4,446,133
[45] May 1, 1984

[54] 1-PHENYL-4-CARBAMOYL PIPERAZINE COMPOUNDS, PROCESS FOR PREPARATION THEREOF AND UTILIZATIONS THEREOF

[75] Inventors: Yutaka Okazaki; Hiroshi Tokuda, both of Chiba; Shiyoichiro Miyahara; Yoshitsugu Yamada, both of Fukuoka, all of Japan

[73] Assignee: Misuitoatsu Chemicals, Inc., Tokyo, Japan

[21] Appl. No.: 235,112

[22] Filed: Feb. 13, 1981

[30] Foreign Application Priority Data

Feb. 15, 1980 [JP] Japan ................. 55-016561

[51] Int. Cl.³ .................. C07D 241/04; A61K 31/495
[52] U.S. Cl. .................................... 424/250; 544/390; 544/392; 544/393
[58] Field of Search ................... 544/390; 424/250

[56] References Cited

U.S. PATENT DOCUMENTS

| | | | |
|---|---|---|---|
| 2,467,895 | 4/1949 | Kushner et al. | 544/390 |
| 2,537,004 | 1/1951 | Breiter et al. | 544/390 |
| 2,643,255 | 6/1953 | Morren | 544/390 |
| 3,133,067 | 5/1964 | Archer | 544/390 |

Primary Examiner—Donald G. Daus
Assistant Examiner—S. A. Gibson
Attorney, Agent, or Firm—Browdy and Neimark

[57] ABSTRACT

The present invention relates to a novel piperazine compound represented by the following general formula (I):

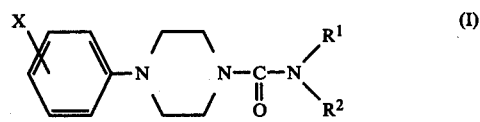

wherein X stands for a hydrogen or halogen atom, an alkoxy, carboxy or alkoxycarbonyl group or a group $R^3CO$— in which $R^3$ stands for an alkyl group having 1 to 4 carbon atoms, $R^1$ stands for a hydrogen atom or an alkyl group, and $R^2$ stands for a hydrogen atom or an alkyl group.

These compounds are valuable as immunopotentiators, such as for the treatment of chronic rheumatoid arthritis and other diseases accompanied by reduction or abnormal change of the immune function.

5 Claims, No Drawings

1-PHENYL-4-CARBAMOYL PIPERAZINE COMPOUNDS, PROCESS FOR PREPARATION THEREOF AND UTILIZATIONS THEREOF

DETAILED DESCRIPTION OF THE INVENTION

The present invention relates to novel piperazine compounds, processes for the preparation thereof and medicinal compositions containing a novel piperazine compound as the active ingredient.

In accordance with the present invention, there is provided a novel piperazine compound represented by the following general formula (I):

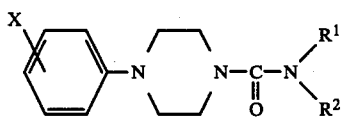

wherein X stands for a hydrogen or halogen atom, an alkoxy, carboxy or alkoxycarbonyl group or a group $R^3CO$— in which $R^3$ stands for an alkyl group having 1 to 4 carbon atoms, $R^1$ stands for a hydrogen atom or an alkyl group, and $R^2$ stands for a hydrogen atom or an alkyl group.

In accordance with the present invention, there also is provided a process for the preparation of novel piperazine compounds represented by the following general formula (I):

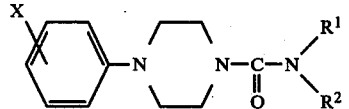

wherein X stands for a hydrogen or halogen atom, an alkoxy, carboxy or alkoxycarbonyl group or a group $R^3CO$— in which $R^3$ stands for an alkyl group having 1 to 4 carbon atoms, $R^1$ stands for a hydrogen atom or an alkyl group, and $R^2$ stands for a hydrogen atom or an alkyl group, which comprises condensing a 1-aryl-4-chlorocarbonylpiperazine represented by the following general formula (II):

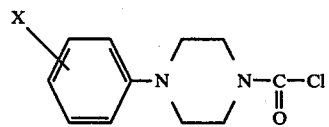

wherein X is as defined above, with an amine represented by the following general formula (III):

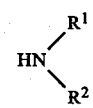

wherein $R^1$ and $R^2$ are as defined above.

Furthermore, in accordance with the present invention, there is provided a process for the preparation of novel piperazine compounds represented by the following general formula (I):

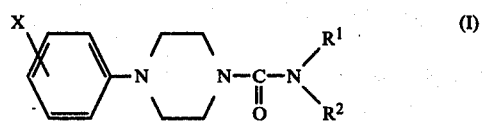

wherein X stands for a hydrogen or halogen atom, an alkoxy, carboxy or alkoxycarbonyl group or a group $R^3CO$— in which $R^3$ stands for an alkyl group having 1 to 4 carbon atoms, $R^1$ stands for a hydrogen atom or an alkyl group, and $R^2$ stands for a hydrogen atom or an alkyl group, which comprises condensing a 1-arylpiperazine represented by the following general formula (IV):

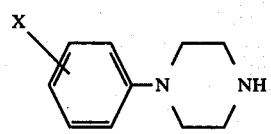

wherein X is as defined above, with a carbamoyl chloride represented by the following general formula (V):

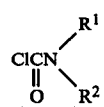

wherein $R^1$ and $R^2$ are as defined above.

Moreover, in accordance with the present invention, there is provided an immunoactive agent which comprises as the active ingredient a novel piperazine compound represented by the following general formula (I):

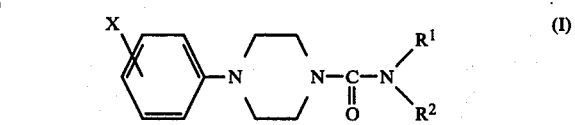

wherein X stands for a hydrogen or halogen atom, an alkoxy, carboxy or alkoxycarbonyl group or a group $R^3CO$— in which $R^3$ stands for an alkyl group having 1 to 4 carbon atoms, $R^1$ stands for a hydrogen atom or an alkyl group, and $R^2$ stands for a hydrogen atom or an alkyl group.

This immunopotentiator is used for the treatment of chronic rheumatoid arthritis and and other diseases accompanied by reduction or abnormal change of the immune function. The novel piperazine compound is obtained by the reaction represented by the following reaction formula:

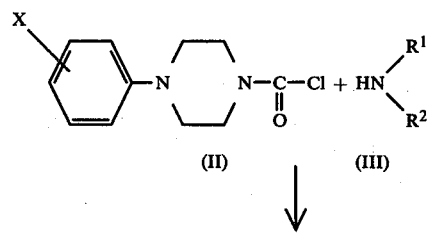

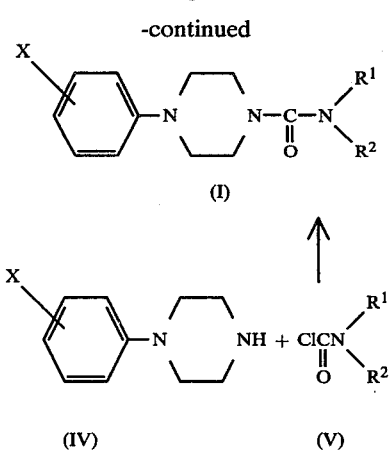

More specifically, the novel piperazine compound of the present invention is obtained by condensing a 1-aryl-4-chlorocarbonylpiperazine represented by the above general formula (II) in which X is as defined above with respect to the general formula (I) with an amine of the above general formula (III) in which $R^1$ and $R^2$ are as defined above with respect to the general formula (I), if desired, in a solvent inactive to the reaction, such as methylene chloride, chloroform, benzene or toluene. The reaction is carried out at about 0° to about 120° C. and the reaction is substantially completed in 1 to 5 hours.

Furthermore, the novel piperazine compound of the present invention represented by the above general formula (I) is obtained by condensing a 1-arylpiperazine represented by the above general formula (IV) in which X is as defined above with respect to the general formula (I) with a carbamoyl chloride represented by the above general formula (V) in which $R^1$ and $R^2$ are as defined above with respect to the general formula (I).

The compound of the general formula (I), obtained by the above reaction, may be isolated and purified according to an usual method, for example, a method in which the reaction mixture is extracted with a dilute acid, the extract is made alkaline to release the intended compound and distillation is carried out under reduced pressure. Furthermore, there may be adopted a method in which the product is purified in the form of an acid addition salt and it is then treated with an appropriate alkali to obtain a free base.

The compound of the general formula (II) or (V) may be prepared by a known method, for example, a method comprising reacting a corresponding amino compound with phosgene.

Specific examples of the novel piperazine compound prepared according to the present invention are as follows.

1-Phenyl-4-methylcarbamoylpiperazine, 1-phenyl-4-ethylcarbamoylpiperazine, 1-phenyl-4-n-propylcarbamoylpiperazine, 1-phenyl-4-i-propylcarbamoylpiperazine, 1-phenyl-4-n-butylcarbamoylpiperazine, 1-phenyl-4-i-butyl-carbamoylpiperazine, 1-phenyl-4-dimethylcarbamoylpiperazine, 1-phenyl-4-diethylcarbamoylpiperazine, 1-phenyl-4-di-i-propylcarbamoylpiperazine, 1-phenyl-4-i-butylpropylcarbamoylpiperazine, N-methyl-N-ethyl-1-phenyl-4-piperazine-carboxamide, N-methyl-N-i-propyl-1-phenyl-4-piperazine-carboxamide, 1-(2-chlorophenyl)-4-diethylcarbamoylpiperazine, 1-(3-chlorophenyl)-4-diethylcarbamoylpiperazine, 1-(4-chlorophenyl)-4-diethylcarbamoylpiperazine, 1-(4-bromophenyl)-4-diethylcarbamoylpiperazine, 1-(4-flucrophenyl)-4-diethylcarbamoylpiperazine, 1-(2-methoxyphenyl)-4-diethylcarbamoylpiperazine, 1-(3-methoxyphenyl)-4-diethylcarbamoylpiperazine, 1-(4-methoxyphenyl)-4-diethylcarbamoylpiperazine, 1-(4-ethoxyphenyl)-4-diethylcarbamoylpiperazine, 1-(4-i-propoxyphenyl)-4-diethylcarbamoylpiperazine, 1-(4-n-butoxyphenyl)-4-diethyl-carbamoylpiperazine, 1-(4-methoxycarbonylphenyl)-4-diethylcarbamoylpiperazine, 1-(4-ethoxycarbonylphenyl)-4-diethylcarbamoylpiperazine, 1-(4-carboxyphenyl)-4-diethylcarbamoylpiperazine and 1-(4-acetylphenyl)-4-diethylcarbamoylpiperazine.

The compound of the present invention represented by the above general formula (I) has pharmacological activities. Highly surprisingly, it was found that the compound of the present invention has a high immunoactive action. The toxicity of the compound is very low. Accordingly, the compound of the present invention is very valuable as a medicine.

This point will now be described in detail with reference to the tests.

Various test systems using animals have been proposed for determining immunopotentiator action. Results of the test of reinforcement of delayed hypersensitivity, which is a typical test among these tests, will now be described.

The delayed hypersensitivity induced when picryl chloride (2-chloro-1,3,5-trinitrobenzene) is coated on the skin of a mouse is known as a typical cellular immunity, and this is one of test systems adopted broadly in the world [see Asherson, G. L. and Ptak, W: Contact and Delayed Hypersensitivity in the Mouse I, Active Sensitization and Passive Transfer, Immunology, 15, 405–416 (1968)].

This system was used for the test of reinforcement of delayed hypersensitivity.

Test 1 (Test of Reinforcement of Delayed Hypersensitivity)

Test Procedures

One group of eight ICR male mice, each having a body weight of about 30 g, were used for the test.

Sensitization was effected by coating a 7% solution of picryl chloride in a 4/1 mixture of olive oil and acetone on the shaved abdomen of the mouse.

Simultaneously with sensitization, a solution or suspension of the compound of the present invention in a 0.2% solution of carboxymethyl cellulose in a physiological saline was orally administered to the mouse at a dose of 50 mg per Kg of the body weight. To the control group, a 0.2% carboxymethyl cellulose solution in a physiological saline was similarly administered.

The delayed hypersensitivity was challenged 7 days after sensitization by gripping the ear of the mouse by a forceps wrapped with a felt impregnated with a 1% solution of picryl chloride in olive oil and coating the ear with the solution. The thickness of the ear was measured before challenging and 24 hours after challenging and the ratio of increase of the thickness (average value of both the ears in eight mice±standard deviation) was obtained as shown in Table 1.

For comparison, the test was similarly carried out by using Levamisole hydrochloride, and the obtained results are shown in Table 1. F.t tests were carried out. The group in which the test result was significant at a level of $P<0.05$ was marked by *, and the group in which the test result was significant at a level of P<0.01 was marked by **.

Results

When the compound of the present invention was administered simultaneously with sensitization, the delayed hypersensitivity caused by challenging was reinforced, and the reinforcing effect was higher than that attained by Levamisole.

Thus, it was confirmed that the compound of the present invention has an activity of activating the cellular immunity response (immunopotentiative action) in mice and this activity is higher than that of Levamisole.

dead cells of Mycobacterium tuberculosis were suspended, and the suspension was injected under the heel skin of the right hind leg. The compound of the present invention was subcutaneously administered 9 times as a whole before and after injection of the adjuvant. The test compound was dissolved in a physiological saline and administered at a dose of 5 mg per Kg of the body weight. The swelling volume of the left hind leg was measured during the period of from the day of injection to the day of completion of the test, and the swelling ratio was calculated. For comparison, the test was similarly conducted by using Levamisole hydrochloride. The obtained results are shown in Table 2. F.t tests were carried out on the obtained test results. The group

TABLE 1

Results of Test of Reinforcement of Delayed Hypersensitivity

| Compound | Ratio of Increase of Ear Thickness (average value ± standard variation, %) |
|---|---|
| control | 29.6 ± 1.9 |
| 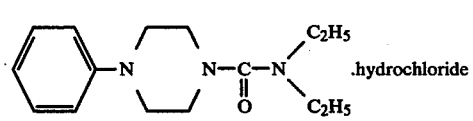 .hydrochloride | 44.0 ± 5.0* |
| 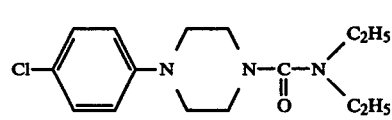 | 42.3 ± 3.7** |
| 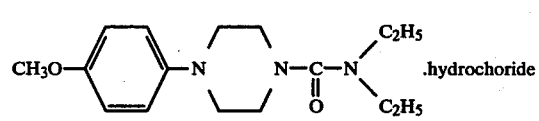 .hydrochoride | 40.1 ± 4.2* |
| 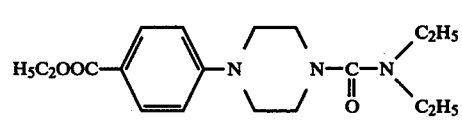 | 39.1 ± 4.0* |
| 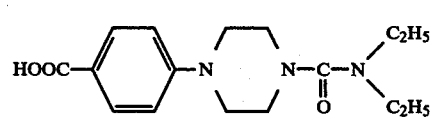 | 37.7 ± 3.0* |
| 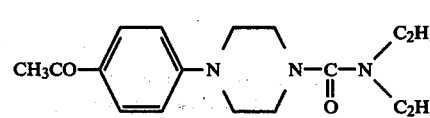 | 38.8 ± 3.5* |
| Levamisole.hydrochloride | 35.6 ± 2.4 |

The adjuvant arthritis in rats caused by injection of a Mycobacterium tuberculosis adjuvant is often utilized for a model test of chronic rheumatoid arthritis in men.

The mechanism of manifestation of this disease has not completely been elucidated, but it is known that the cellular immunity takes an important role. The immunopotentiative action of the compound of the present invention was tested according to this known adjuvant arthritis test.

Test 2 (Adjuvant Arthritis Test, Table 2)

Test Procedures

A group of ten 9-weeks-old SD male rats were used for the test. In 0.1 ml of fluid paraffin, 0.4 mg of dry in which the test result was significant at a level of P<0.05 was marked by *, and the group in which the test result was significant at a level of P<0.01 was marked **.

Results

The secondary inflammation of the adjuvant arthritis was remarkably controlled by the compounds of the present invention, and the effect was statistically significant with respect to the control group to which no compound was administered. The effect by the compound of the present invention was higher than that of Levamisole used as the reference compound but there is no statistically significant difference between the two compounds. Thus, it was confirmed that the compound of the present invention has an immunomodulating activity and an anti-arthritic activity and these activities are higher than those of Levamisole.

tized by the macrophage. Accordingly, the macrophage is very important for immunotherapy of cancers.

The results of the test of the action of the effective ingredient of the present invention on the macrophage will now be described with reference to the following Test 3. More specifically, the separated macrophage

TABLE 2
Results of Adjuvant Arthritis Test

| Compound | Swelling Ratio (average value ± standard variation, %) | | |
|---|---|---|---|
| | 15 days | 18 days | 21 days |
| control | 84.4 ± 9.0 | 103.2 ± 9.7 | 107.5 ± 13.3 |
| C₆H₅—N(piperazine)—C(=O)—N(C₂H₅)₂ .hydrochloride | 47.0 ± 8.0** | 52.4 ± 9.2** | 59.8 ± 12.1* |
| Cl—C₆H₄—N(piperazine)—C(=O)—N(C₂H₅)₂ | 57.9 ± 11.1 | 55.7 ± 9.7** | 62.8 ± 10.9* |
| CH₃O—C₆H₄—N(piperazine)—C(=O)—N(C₂H₅)₂ .hydrochloride | 60.1 ± 11.3 | 57.1 ± 8.8** | 64.4 ± 10.5* |
| H₅C₂OOC—C₆H₄—N(piperazine)—C(=O)—N(C₂H₅)₂ | 63.7 ± 12.0 | 60.4 ± 9.2** | 66.9 ± 11.1* |
| HOOC—C₆H₄—N(piperazine)—C(=O)—N(C₂H₅)₂ | 65.0 ± 10.2 | 64.6 ± 7.9** | 70.8 ± 10.7* |
| CH₃CO—C₆H₄—N(piperazine)—C(=O)—N(C₂H₅)₂ .hydrochloride | 61.4 ± 10.4 | 62.2 ± 8.8** | 68.4 ± 12.0* |
| Levamisole.hydrochloride | 65.2 ± 5.9 | 69.3 ± 7.1* | 80.7 ± 9.6 |

As illustrated in Tests 1 and 2, the compound of the present invention is very effective as an immunopotentiator, and therefore, the compound of the present invention is effective for remedy of diseases accompanied by reduction or abnormal change of the immune functions, for example, auto-immune diseases such as chronic rheumatoid arthritis.

As the immunotherapy of cancers, there can be considered the method in which a specific or non-specific immunity reduced by the cancer-bearing state is increased by some reaction or other and the resistance to cancer is given to the living body for remedy of cancer. Participation of macrophage in such reaction is indispensable. More specifically, (1) the activated macrophage has a cancer cell-mediating cytotoxicity, (2) the macrophage is one of influential effector cells for the antibody-dependent cell-mediating cytotoxicity, and (3) when a specific immunity to cancer cells is established and killer T cells are induced, the cancer antigen on the cancer cells should be transferred to the T cells and recognized as the antigen. For this purpose, the cancer cells mediated by the reactions (1) and (2) are phagocytized by the macrophage. Accordingly, the macrophage is very important for immunotherapy of cancers.

and EL-4 leukemic cell were mixed and cultured, and $^3$H-thymidine was added to a culture medium and the quantity of $^3$H-thymidine incorporated into the EL-4 cell was determined to examine the activity of the macrophage. When the macrophage is activated by administration of the effective ingredient of the present invention, inhibition of the growth of EL-4 cell, that is, phagocytosis of the cancer cell by the macrophage, is observed. Accordingly, if the take-in amount of $^3$H-thymidine is measured and this amount is reduced, it is confirmed that the macrophage has been activated.

Test 3 (In-Vitro Test of Inhibition of Growth of Cancer Cell) by Macrophage

Test Procedures

To a group of three ddY female mice (having a body weight of 25 g), 0.5 ml of a suspension of 2 mg of the effective ingredient of the present invention in 5 ml of a physiological saline solution was intraperitoneally administered. The dose was 8 mg per Kg of the body weight. To the control group, a physiological saline solution was similarly administered. After passage of 4 days, exuded abdominal cells were collected and deposited on a plastic Petri dish to collect macrophages.

Then, $1 \times 10^6$ of so obtained macrophages and $1 \times 10^5$ of EL-4 leukemic cells of C57 BL/6J mouse were mixed and cultured in an RPMI 1640 culture medium to which 10% of bovine embryo serum was added (at 37° C. in the presence of 5% of $CO_2$) for 24 hours. Then, $0.1\mu$ Ci of $^3$H-thymidine was added and culturing was further conducted for 16 hours. Cells were collected on a filter paper from the culture medium and the amount of $^3$H-thymidine taken in was determined by a liquid scintillation counter. The take-in ratio (%) was calculated according to the following formula:

Take-in ratio (%) =

$$\frac{\text{(count number in case of mixed culturing)} - \text{(count number in case of single culturing of macrophages)}}{\text{(count number of single culturing of EL-4 cells)}} \times 100\%$$

The average value (%) in one group of three mice was determined to obtain results shown in Table 3. For comparison, the test was similarly carried out by using Levamisol hydrochloride.

Results

It was confirmed that the effective ingredient of the present invention prominently inhibits take-in of $^3$H-thymidine by EL-4 leukemic cells while Levamisole hydrochloride does not exhibit such action.

More specifically, it was confirmed that the effective ingredient of the present invention activates the macrophage to cause phagocytosis of cancer cells, whereas Levamisole hardly exhibits such action.

TABLE 3

| Compound | Take-in Ratio (average value, %) |
|---|---|
| control | 80.2 |
| 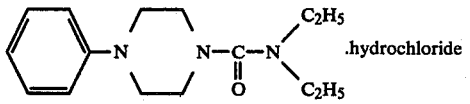 | 24.4 |
| 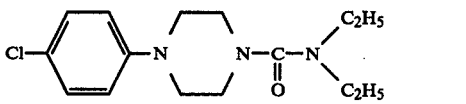 | 20.5 |
|  | 27.7 |
| 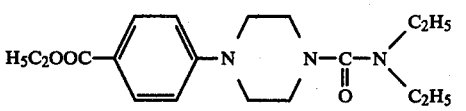 | 30.3 |
| 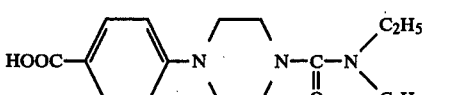 | 29.8 |
| 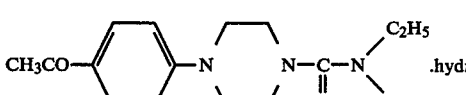 | 27.4 |
| Levamisole.hydrochloride | 49.0 |

The results of treatment of certain cancers of animals by the effective ingredient of the present invention will now be described with reference to the following Tests 4 and 5.

Test 4 (Test of Antitumor Effect to Sarcoma 180 by Oral Administration)

Test Procedures

One group of 6 ICR female mice were intradermally inoculated with $2 \times 10^6$ of Sarcoma 180 cells, and during a period of 10 days after passage of 24 hours, a solution or suspension of the effective compound in a physiological saline solution was orally administered at a dose of 0.1 ml per 10 g of the body weight once a day. To the control group, a physiological saline solution was similarly administered. The dose of the compound was 100 mg per Kg of the body weight. The diameter D (mm) of the tumor was measured, and the average value and the number N of the living mice were determined to obtain results shown in Table 4.

Results

The inoculated tumor cells were propagated and grew into solid tumors. However, if the effective ingredient of the present invention was orally administered repeatedly the tumor was diminished in size or disappeared.

For comparison, the test was similarly carried out by using Levamisole hydrochloride, but no substantial carcinostatic action was observed.

was subcutaneously administered and the dose was changed to 20 mg per Kg off the body weight.

Results:

The change of the diameter D (mm) of the tumor was examined and the number of living mice was checked to obtain results shown in Table 5. Even if the dose was 1/5 of the dose adopted in case of oral administration, the same effect as obtained by oral administration could be obtained. In contrast, Levamisole hydrochloride had no substantial carcinostatic activity.

TABLE 4

Test of Carcinostatic Effect to Sarcoma 180 by Oral Administration

| Compound | Item | 0 | 2 | 4 | 6 | 8 | 10 |
|---|---|---|---|---|---|---|---|
| control | D | — | 10.6 | 15.2 | 22.4 | 31.5 | 37.6 |
|  | N | 6 | 6 | 6 | 6 | 5 | 1 |
| 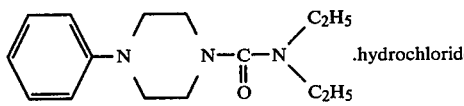 | D | — | 7.8 | 6.6 | 3.7 | 0.9 | 0 |
|  | N | 6 | 6 | 6 | 6 | 6 | 6 |
| 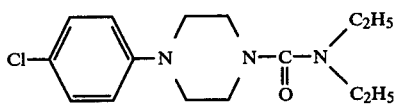 | D | — | 7.1 | 5.8 | 3.0 | 0 | 0 |
|  | N | 6 | 6 | 6 | 6 | 6 | 6 |
| 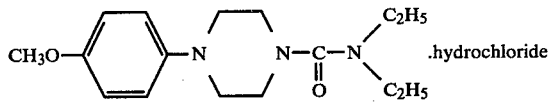 | D | — | 8.1 | 4.6 | 5.0 | 2.2 | 0.6 |
|  | N | 6 | 6 | 6 | 6 | 6 | 6 |
| 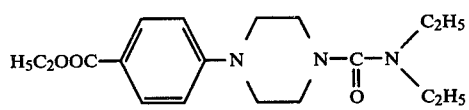 | D | — | 9.2 | 7.4 | 4.8 | 3.2 | 0 |
|  | N | 6 | 6 | 6 | 6 | 6 | 6 |
| 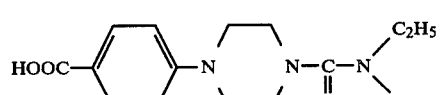 | D | — | 6.8 | 3.5 | 4.4 | 2.2 | 0 |
|  | N | 6 | 6 | 6 | 6 | 6 | 6 |
| 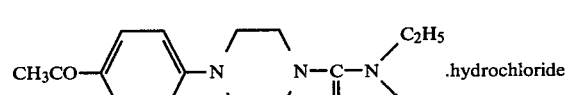 | D | — | 8.4 | 4.7 | 5.1 | 6.6 | 0 |
|  | N | 6 | 6 | 6 | 6 | 6 | 6 |
| Levamisole.hydrochloride | D | — | 10.2 | 16.2 | 20.7 | 29.6 | 28.1 |
|  | N | 6 | 6 | 6 | 6 | 6 | 3 |

Note
D: average diameter (mm) of tumor
N: Number of living mice

Test 5 (Test of Antitumor Effect to Sarcoma 180 by subcutaneous Administration)

Test Procedures the test was carried out in the same manner as described in Test 4 except that the effective compound

TABLE 5

Test of Antitumor Effect to Sarcoma 180 by Subcutaneous Administration

| Compound | Item | 0 | 2 | 4 | 6 | 8 | 10 |
|---|---|---|---|---|---|---|---|
| control | D | — | 10.8 | 16.6 | 20.3 | 31.3 | 40.5 |
|  | N | 6 | 6 | 6 | 6 | 4 | 1 |

TABLE 5-continued

Test of Antitumor Effect to Sarcoma 180 by Subcutaneous Administration

| Compound | Item | 0 | 2 | 4 | 6 | 8 | 10 |
|---|---|---|---|---|---|---|---|
| 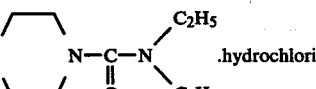 | D<br>N | —<br>6 | 2.9<br>6 | 4.1<br>6 | 4.8<br>6 | 1.0<br>6 | 0<br>6 |
| 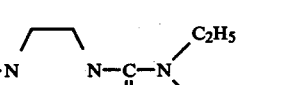 | D<br>N | —<br>6 | 2.3<br>6 | 2.1<br>6 | 3.8<br>6 | 0<br>6 | 0<br>6 |
| 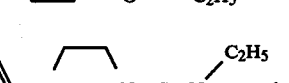 | D<br>N | —<br>6 | 3.0<br>6 | 1.0<br>6 | 2.2<br>6 | 5.3<br>6 | 4.0<br>6 |
| 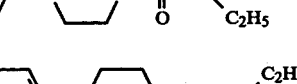 | D<br>N | —<br>6 | 3.2<br>6 | 3.4<br>6 | 3.8<br>6 | 2.5<br>6 | 0.8<br>6 |
| 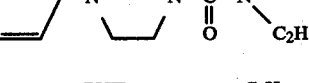 | D<br>N | —<br>6 | 2.1<br>6 | 4.4<br>6 | 4.8<br>6 | 3.9<br>6 | 0<br>6 |
| 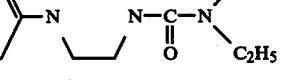 | D<br>N | —<br>6 | 4.1<br>6 | 7.7<br>6 | 8.5<br>6 | 4.3<br>6 | 0<br>6 |
| Levamisole.hydrochloride | D<br>N | —<br>6 | 7.7<br>6 | 14.8<br>6 | 14.4<br>6 | 30.2<br>3 | 31.6<br>2 |

Note
D: average diameter (mm) of tumor
N: number of living mice

The toxicity of the effective compound of the present invention will now be described with reference to the following Test 6.

Test 6 (Test of Acute Toxicity by Oral Administration)

Test Procedures

A solution or suspension of the compound in a physiological saline solution was orally administered to one group of three ddY male mice, and after 7 days, the estimated $LD_{50}$ value was determined.

Results:

The estimated $LD_{50}$ value of the effective ingredient according to the present invention was in the range of from 600 to 1500 mg/Kg, which is much larger than the estimate $LD_{50}$ value of Levamisole hydrochloride, which was in the range of from 150 to 200 mg/Kg. Accordingly, it was confirmed that the toxicity of the compound of the present invention is very low.

When the compound of the present invention is used as a medicine, it may be used in the form of a free base. However, in view of the stability and easiness in formulation of a medicine, it is preferred that the compound be used in the form of a pharmaceutically acceptable salt such as a hydrochloride, a citrate or a phosphate, especially when water solubility is required as in case of an injection.

The compound of the present invention can be administered in the form of a customary formulation according to a customary method adopted for conventional immunopotentiator agents. For example, as the preparation for oral administration, there can be mentioned a capsule, a granule, a pill, a fine granule, a tablet and a syrup. Furthermore, a suppository is suitable for direct administration to the rectum. Moreover, an injection for intravenous administration, subcutaneous administration or intramuscular administration may be used.

The immunopotentiator of the present invention may be used for remedy of diseases accompanied by reduction or abnormal change of the immunizing function, for example, auto-immune diseases such as chronic rheumatoid arthritis and multiple myositis, various infectious diseases. Recovery or normalization of the immunizing function of patients suffering from these diseases can be expected by administration of the compound of the present invention. Mitigation of subjective symptoms and objective symptoms can be expected by administration of the compound of the present invention.

The administration method and preparation form may appropriately be chosen according to the kind of the disease and the condition of the patient. In case of oral administration, the dose of the compound of the present invention is 1 to 100 mg, preferably 1 to 20 mg, per Kg of the body weight per day. In case of administration to the rectum, the dose is preferably 1 to 100 mg per Kg of the body weight per day, in case of intravenous administration, the dose is preferably 1 to 10 mg per Kg of the body weight per day, and in case of subcutaneous or intramuscular administration, the dose is preferably 1 to 30 mg per Kg of the body weight.

It is preferred that the dose be appropriately adjusted according to the kind of the disease and the condition of the patient. The effect of the active compound of the present invention can be increased by using other medicines in combination appropriately according to the kind of the disease and the condition of the patient.

Medicines of the compound of the present invention can be prepared according to the customary formula and method adopted for ordinary immunopotentiator agents.

The present invention will now be described in detail with reference to the following Examples.

Example 1 (1-phenyl-4-diethylcarbamoylpiperazine)

In 70 ml of chloroform was dissolved 12.0 g (0.074 mole) of 1-phenylpiperazine at room temperature, and a solution of 10.9 g (0.08 mole) of diethylcarbamoyl chloride in 30 ml of chloroform was dropped to the above solution over a period of 30 minutes. Then, the mixture was stirred at 40° C. for 5 hours and then cooled. The precipitated white crystal was removed, and the filtrate was concentrated under reduced pressure and 50 ml of a 25% aqueous solution of sodium hydroxide was added. The mixture was extracted 2 times with 50 ml of benzene and dried with anhydrous sodium sulfate. The solvent was removed by distillation to obtain crude 1-phenyl-4-diethylcarbamoylpiperazine as the residue. By distillation under reduced pressure, 5.7 g of a purified product having a boiling point of 180.5° C. at 2.3 mm Hg was obtained. The yield was 29.5%. The elementary analysis values are as follows.

Found: C=68.74%, H=8.94%, N=15.70%. Anal. Calcd for $C_{15}H_{23}N_3O$: C=68.93%, H=8.87%, N=16.08%.

Example 2 (1-phenyl-4-diethylcarbamoylpiperazine hydrochloride)

In 50 ml of chloroform was dissolved 2.6 g (0.01 mole) of 1-phenyl-4-diethylcarbamoylpiperazine at room temperature, and the solution was saturated with gaseous hydrogen chloride and stirred for a certain time. The solvent was removed by distillation under reduced pressure. Then, 50 ml of acetone was added to the residue and the mixture was stirred for a certain time. The precipitated crystal was recovered by filtration, washed with acetone, stirred in 50 ml of acetone to effect washing and dried to obtain 2.1 g of 1-phenyl-4-diethylcarbamoylpiperazine hydrochloride having a melting point of 190° to 192° C. The yield was 70.9%. The elementary analysis values are as follows.

Found: C=60.63%, H=8.24%, N=14.09%, Cl=11.93%. Anal. Calcd for $C_{15}H_{24}N_3OCl$: C=60.49%, H=8.12%, N=14.11%, Cl=11.91%.

Example 3
[1-(4-chlorophenyl)-4-diethylcarbamoylpiperazine]

In 40 ml of methylene chloride was dissolved 4.0 g (0.02 mole) of 1-(4-chlorophenyl)piperazine at room temperature. Then, a solution of 3.0 g (0.022 mole) of diethylcarbamoyl chloride in 30 ml off methylene chloride was dropped to the above solution over a period of 30 minutes and the mixture was stirred for 4 hours at room temperature. The precipitate was removed and the filtrate was made alkaline by addition of 30 ml of a 35% aqueous solution of sodium hydroxide and extracted with 50 ml of methylene chloride. The organic layer was dried with anhydrous sodium sulfate and the solvent was removed by distillation under reduced pressure to obtain crude 1-(4-chlorophenyl)-4-diethylcarbamylpiperazine as the residue. The low-boiling-point component was removed by distillation under reduced pressure and the residue was recrystallized from n-hexane to obtain 1.8 g of a purified product having a melting point of 63° to 64° C. The yield was 29.9%. The elementary analysis values are as follows.

Found: C=60.56%, H=7.70%, N=13.96%, Cl=11.68%. Anal. Calcd for $C_{15}H_{22}N_3ClO$: C=60.89%, H=7.51%, N=14.21%, Cl=11.98%.

Example 4
[1-(4-methoxyphenyl)-4-diethylcarbamoylpiperazine]

In 75 ml of chloroform was dissolved 10.4 g (0.054 mole) of 1-(4-methoxyphenyl)piperazine at room temperature, and a solution of 7.4 g (0.054 mole) of diethylcarbamoyl chloride in 50 ml of chloroform was dropped to the above solution over a period of 30 minutes. The mixture was stirred at 50° C. for 2 hours, and the insoluble substance was removed, and the filtrate was concentrated under reduced pressure and 100 ml of a 35% aqueous solution of sodium hydroxide and 300 ml of ether were added to the concentrate. The mixture was stirred for a certain time, and the ether layer was dried with anhydrous sodium sulfate and the solvent was removed by distillation under reduced pressure, and the residue was purified by silica gel chromatography and distillation under reduced pressure to obtain 7.4 of purified 1-(4-methoxyphenyl)-4-diethylcarbamoylpiperazine having a boiling point 195° C. at 0.5 mm Hg. The yield was 47.0%. Elementary analysis values are as follows.

Found: C=65.71%, H=8.77%, N=14.38%. Anal. Calcd for $C_{16}H_{25}N_3O_2$: C=65.95%, H=8.65%, N=14.42%.

Example 5
[1-(4-methoxyphenyl)-4-diethylcarbamoylpiperazine hydrochloride]

In 50 ml of chloroform was dissolved 2.9 g (0.01 mole) of 1-(4-methoxyphenyl)-4-diethylcarbamoylpiperazine, and the solution was saturated with gaseous hydrogen chloride and stirred at 40° C. for 3 hours. The solvent was removed by distillation under reduced pressure. The residue was mixed with 30 ml of a mixed solvent of ethyl acetate and methanol. The insoluble substance was removed, and the precipitated crystal was recovered by filtration to obtain 1.7 g of 1-(4-methoxyphenyl)-4-diethylcarbamoylpiperazine hydrochloride having a melting point of 174° to 184° C. The yield was 52.1%. The elementary analysis values are as follows.

Found: C=58.00%, H=7.96%, N=12.57%, Cl=10.59%. Anal. Calcd for $C_{16}H_{26}N_3O_2Cl$: C=58.61%, H=7.99%, N=12.82%, Cl=10.82%.

Example 6
[1-(4-ethoxycarbonylphenyl)-4-diethylcarbamoylpiperazine]

In 90 ml of chloroform was dissolved 3.6 g (0.0152 mole) of 1-(4-ethoxycarbonylphenyl)piperazine at room temperature. The temperature was elevated at 50° C. and a solution of 1.54 g (0.0114 mole) of diethylcarbamoyl chloride in 45 ml of chloroform was dropped to the above solution over a period of 30 minutes. The mixture was heated and refluxed for 2 hours, and the insoluble substance was removed and the filtrate was subjected to distillation under reduced pressure. The residue was mixed with 50 ml of a 35% aqueous solution of sodium hydroxide, and 200 ml of toluene was added and the mixture was stirred at room temperature for 30 minutes. The water layer was removed, and the organic layer was dried with anhydrous sodium sulfate and the solvent was removed by distillation under reduced pressure. The residue was mixed with 20 ml of benzene and the mixture was stirred for a certain time. The benzene-insoluble substance was removed and the filtrate was subjected to silica gel chromatography to obtain 3.6 g of 1-(4-ethoxycarbonylphenyl)-4-diethylcarbamoylpiperazine having a melting point of 77° to 82° C.

The elementary analysis values are as follows.
Found: C=64.82%, H=8.34%, N=12.53%. Anal. Calcd for $C_{18}H_{27}N_3O_3$: C=64.84%, H=8.16%, N=12.60%.

Example 7
[1-(4-carboxyphenyl)-4-diethylcarbamoylpiperazine]

To 3.3 g (0.01 mole) of 1-(4-ethoxycarbonylphenyl)-4-diethylcarbamoylpiperazine obtained in Example 6 were added 90 ml of ethanol, 10 ml of water and 1.0 g of sodium hydroxide, and the mixture was heated and refluxed under stirring for 3.5 hours. The solvent was removed by distillation under reduced pressure, and 100 ml of water was added to the residue and the insoluble substance was removed. The pH value of the filtrate was adjusted to 3 by 2 N hydrochloric acid. The precipitate was recovered by filtration and dissolved in a dilute aqueous solution of sodium hydroxide, and the pH value was adjusted to 3 again by 2 N hydrochloric acid. The precipitate was recrystallized from methanol to obtain 1.5 g of 1-(4-carboxyphenyl)-4-diethylcarbamoylpiperazine having a melting point of 207° to 209.5° C. The elementary analysis values are as follows.
Found: C=62.71%, H=7.58%, N=13.79%. Anal. Calcd for $C_{16}H_{23}N_3O_3$: C=62.93%, H=7.59%, N=13.76%.

Example 8
[1-(4-acetylphenyl)-4-diethylcarbamoylpiperazine and its hydrochloride]

In 50 ml of chloroform was dissolved 10.2 g (0.05 mole) of 1-(4-acetylphenyl)-piperazine at room temperature, and 6.8 g (0.05 mole) of diethylcarbamoyl chloride was dropped to the solution over a period of 30 minutes. The mixture was stirred at room temperature for 5 hours, and the insoluble substance was removed. The filtrate was subjected to distillation under reduced pressure and the residue was made alkaline by 4 N aqueous solution of sodium hydroxide and extracted with 100 ml of toluene. The organic layer was dried with anhydrous sodium sulfate and the solvent was removed by distillation under reduced pressure. The residue was recrystallized from a benzene-hexane mixed solvent to obtain 1-(4-acetylphenyl)-4-diethylcarbamoylpiperazine having a boiling point of 72° to 76° C. The so obtained free base was dissolved in chloroform, and the solution was saturated with gaseous hydrogen chloride and stirred for a certain time. Then, the solution was subjected to a post treatment according to customary procedures to obtain 8.6 g of 1-(4-acetylphenyl)-4-diethylcarbamoylpiperazine hydrochloride having a melting point of 145° to 152° C.

The elementary analysis values are as follows.
Found: C=59.89%, H=7.76%, N=12.28%, Cl=10.38%. Anal. Calcd for $C_{17}H_{26}N_3O_2Cl$: C=60.07%, H=7.71%, N=12.37%, Cl=10.43%.

Example 9 [tablets containing 1-phenyl-4-diethylcarbamoylpiperazine hydrochloride as effective ingredient]

A mixture of 50 g of 1-phenyl-4-diethylcarbamoylpiperazine hydrochloride, 38 g of lactose, 35 g of corn starch of 20 g of crystalline cellulose was sufficiently stirred, and the mixture was kneaded and granulated with a solution of 5 g of hydroxypropyl cellulose in 100 ml of water and dried at 50° C. for 4 hours. The granulated mixture was mixed with 2 g of magnesium stearate and formed into tablets, each having a weight of 150 mg, by a tableting machine.

Example 10 [capsules containing 1-(4-chlorophenyl)-4-diethylcarbamoylpiperazine as effective ingredient]

A mixture of 100 g of 1-(4-chlorophenyl)-4-diethylcarbamoylpiperazine, 94 g of lactose, 60 g of corn starch 40 g of crystalline cellulose and 6 g of magnesium stearate was sufficiently stirred and filled into hard capsules in an amount of 300 mg per capsule by using an encapsulating machine.

Example 11 [granules containing 1-(4-ethoxycarbonylphenyl)-4-diethylcarbamoylpiperazine as effective ingredient]

A mixture of 100 g of 1-(4-ethoxycarbonylphenyl)-4-diethylcarbamoylpiperazine, 152 g of lactose, 140 g of corn starch and 80 g of crystalline cellulose was sufficiently stirred, and the mixture was kneaded and granulated with a solution of 20 g of hydroxypropyl cellulose in 400 ml of water and dried at 50° C. for 4 hours. The granules were passed through a 12-mesh screen to effect classification, and the granules were mixed with 8 g of magnesium stearate and the mixture was sufficiently stirred to obtain granules.

Example 12 [suppository containing 1-(4-carboxyphenyl)-4-diethylcarbamoylpiperazine as effective ingredient]

A mixture of 10 g of 1-(4-carboxyphenyl)-4-diethylcarbamoylpiperazine and 90 g of Witepsol ®W-35 (Dynamill Novel Chemicals, West Germany) were heated and molten at 60° C., and the melt was cast into molds so that the weight of each suppository was 1.5 g or 3 g. The cast melt was cooled and solidified to obtain suppositories.

Example 13 [injections containing 1-(4-methoxyphenyl)-4-diethylcarbamoylpiperazine hydrochloride as effective ingredient]

A mixture of 10 g of 1-(4-methoxyphenyl)-4-diethylcarbamoylpiperazine hydrochloride and 0.4 g of sodium chloride was dissolved in an appropriate amount of distilled water for injections so that the total amount was 100 ml. The so formed injection was suitable for intravenous administration.

Example 14 [injections containing 1-(4-acetylphenyl)-4-diethylcarbamoylpiperazine hydrochloride as effective ingredient]

A mixture of 10 g of 1-(4-acetylphenyl)-4-diethylcarbamoylpiperazine hydrochloride and 0.4 g of sodium chloride was dissolved in an appropriate amount of distilled water for injections so that the total amount was 100 ml. The so formed injection was suitable for intravenous administration.

What is claimed is:

1. A piperazine compound represented by the following formula or its inorganic or oganic acid salt:

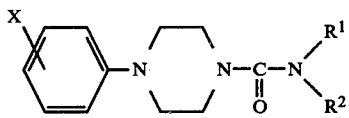

wherein X stands for a carboxy or alkoxycarbonyl group, R¹ stands for a hydrogen atom or an alkyl group, and R² stands for a hydrogen atom or an alkyl group.

2. A compound as set forth in claim 1, wherein X is an ethoxycarbonyl group and each of R¹ and R² is an ethyl group.

3. A compound as set forth in claim 1, wherein X is a carboxyl group and each of R¹ and R² is an ethyl group.

4. A compound as set forth in claim 1, wherein X is carboxy, methoxycarbonyl or ethoxycarbonyl, R¹ stands for a hydrogen atom or a $C_{1-4}$ alkyl group, and R² stands for a hydrogen atom or a $C_{1-4}$ alkyl group.

5. A method for the treatment of chronic rheumatoid arthritis, comprising administering to a patient having said disease an immunopotentiating amount of a compound represented by the following formula:

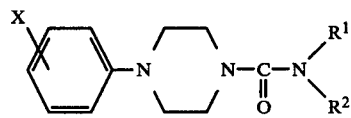

wherein X stands for a hydrogen or halogen atom, a $C_{1-4}$ alkoxy, carboxy, methoxycarbonyl, or ethoxycarbonyl group or the group $R^3CO-$ in which R³ stands for a $C_{1-4}$ alkyl group, R¹ stands for a hydrogen atom or a $C_{1-4}$ alkyl group, and R² stands for a hydrogen atom or a $C_{1-4}$ group, in the form of a free base or a physiologically acceptable acid addition salt.

* * * * *